United States Patent
Mori et al.

(10) Patent No.: US 7,288,397 B2
(45) Date of Patent: Oct. 30, 2007

(54) NICOTIANAMINE AMINOTRANSFERASE AND GENE THEREFOR

(75) Inventors: Satoshi Mori, Narashino (JP); Hiromi Nakanishi, Tokyo (JP); Michiko Takahashi, Utsunomiya (JP)

(73) Assignee: Sumitomo Chemical Company, Limited, Osaka (JP)

( * ) Notice: Subject to any disclaimer, the term of this patent is extended or adjusted under 35 U.S.C. 154(b) by 26 days.

(21) Appl. No.: 11/013,391

(22) Filed: Dec. 17, 2004

(65) Prior Publication Data

US 2005/0095689 A1    May 5, 2005

Related U.S. Application Data

(62) Division of application No. 09/026,400, filed on Feb. 19, 1998, now Pat. No. 6,897,300.

(30) Foreign Application Priority Data

Feb. 21, 1997    (JP)    ............................. 9-037499

(51) Int. Cl.
C12N 9/10    (2006.01)
C12N 15/82    (2006.01)
C12N 1/00    (2006.01)
C12N 5/04    (2006.01)

(52) U.S. Cl. ................ 435/193; 435/69.1; 435/243; 435/320.1; 435/419; 536/23.2

(58) Field of Classification Search ............... 435/193, 435/243, 69.1, 320.1; 536/23.1, 23
See application file for complete search history.

(56) References Cited

OTHER PUBLICATIONS

Takahashi et al., Abstr. of XIII Int'l. Plant Nutrition Colloquium, Tokyo, Japan (Sep. 13-19, 1997).
Takahashi et al., Abstr. Paper of Meeting of Japanese Society of Plant Physiologists, Kyoto University, Japan (Mar. 27-29, 1997) (English Translation).
Takahashi et al., Abstr. Paper of Meeting of Japanese Society of Soil Science and Plant Nutrition, Shizuoka, Japan (Apr. 2-4, 1997) (English Translation).
Takahashi et al., Abstr. Paper of 9th Int'l. Symposium on Iron Nutrition and Interactions in Plants, Hohenheim University, Germany (Jul. 20-25, 1997).
Shojima et a., Plant Cell Physiol., vol. 30, No. 5, pp. 673-677 (1989).
Shojima et al., Plant Physiol., vol. 93, pp. 1497-1503 (1990).
Ohata et al., Soil Sci. Plant Nutr., vol. 39, No. 4, pp. 745-749 (1993).
Kanazawa et al., J. Exper. Botany, vol. 45, No. 281, pp. 1903-1906 (Dec. 1994).
Kanazawa et al., J. Abadia (ed.) Iron Nutrition in Soils and Plants, pp. 37-41 (1995).
Kanazawa et al., J. Exper. Botany, vol. 46, No. 290, pp. 1241-1244 (Sep. 1995).
S. Mori, Soil Sci. Plant Nutr., vol. 43, pp. 975-980 (1997).
Takahashi et al., Plant nutrition for sustainable food production and environment. T. Ando. eds. Kluwer Academic Press. Doordrecht, pp. 279-280 (1997).

Primary Examiner—Rebecca E. Prouty
Assistant Examiner—Md Younus Meah
(74) Attorney, Agent, or Firm—Birch, Stewart, Kolasch & Birch, LLP

(57) ABSTRACT

A protein having an amino acid sequence represented by SEQ ID NO: 2 or 4 or an amino acid sequence having said amino acid sequence with a single or plural amino acids deleted, replaced or added, and having the nicotianamine aminotransferase activity, a gene encoding said protein as well as utilization thereof for enhancement of ability of absorbing insoluble iron in soil and for improvement of resistance to iron deficiency are provided.

5 Claims, No Drawings

NICOTIANAMINE AMINOTRANSFERASE AND GENE THEREFOR

This application is a Divisional of application Ser. No. 09/026,400, filed on Feb. 19, 1998, now U.S. Pat. No. 6,897,300 and for which priority is claimed under 35 U.S.C. § 120; and this application claims priority of Application No. 09-037499 filed in Japan on Feb. 21, 1997 under 35 U.S.C. § 119; the entire contents of all are hereby incorporated by reference.

BACKGROUND OF THE INVENTION

1. Field of the Invention

The present invention relates to a nicotianamine aminotransferase, a gene therefor and utilization thereof.

2. Description of Related Art

Calcareous soil, a saline illuviation soil in dry ground, occupies about 30% of the soil in the world, including China, the Middle and Near East countries, the Central and North Africa, the Central and West America and soon. In this soil, iron in the soil is insolubilized due to a high pH. A plant can not grow in this soil, developing chlorosis by iron deficiency, unless it can absorb iron in soluble form from the root by any means. When agriculture and environmental afforestation are desired, measures against the deficiency of soluble iron in the soil will be an important problem.

As measures to solve the iron deficiency of plant by agricultural technique, it may be considered (1) to correct pH of the alkaline soil to neutral or slightly acidic one by addition of sulfur, (2) to apply a substance containing a chelated iron or (3) to increase soluble iron in the soil by enhancing soil microorganism activity, for example, by means of application of an organic substance, thereby increasing siderophore (an iron transporter) production by the microorganism.

These means for providing iron by soil treatment, however, are not always satisfactory because there are problems, for example, that a large amount of application material is required, that the effect is very unstable depending on the method of application including time of application, site of application, concentration, kind of spreader or the like and weather conditions. Therefore, development of novel techniques has been demanded.

Under these circumstances, the present inventors have conducted extensive studies and discovered a novel gene which is suitable for enhancing absorption ability on insoluble iron in soil and improving resistance to iron deficiency and thus have completed the present invention.

SUMMARY OF THE INVENTION

Accordingly, the present invention provides:

(1) A protein comprising an amino acid sequence represented by SEQ ID NO: 2 or 4 or an amino acid sequence having said amino acid sequence with a single or plural amino acids deleted, replaced or added, and having the nicotianamine aminotransferase activity (hereinafter, referred to as the protein of the present invention), (2) A gene encoding the protein as defined in the foregoing item 1 (hereinafter, referred to as the gene of the present invention), (3) The gene in accordance with the foregoing item 2 having a nucleotide sequence encoding the amino acid sequence represented by SEQ ID NO: 2 or 4, (4) The gene in accordance with the foregoing item 3 having a nucleotide sequence represented by SEQ ID NO: 1 or 3, (5) A plasmid comprising the gene in accordance with the foregoing item 2 (hereinafter, referred to as the plasmid of the present invention), (6) An expression plasmid comprising (1) a promoter capable of functioning in a host cell, (2) the gene in accordance with the foregoing item 2 and (3) a terminator capable of functioning in a host cell, operably linked in the above described order (hereinafter, referred to as the expression plasmid of the present invention), (7) A process for constructing an expression plasmid, which comprises combining (1) a promoter capable of functioning in a host cell, (2) the gene in accordance with the foregoing item 2 and (3) a terminator capable of functioning in a host cell, operably linked in the above described order (hereinafter, referred to as the process for construction of the present invention), (8) A transformant comprising a host cell harboring the plasmid as defined in foregoing item 5 or 6, (9) The transformant in accordance with the foregoing item 8, wherein the host is a microorganism.

(10) The transformant in accordance with the foregoing item 8, wherein the host cell is a plant cell,

(11) A process for enhancing iron absorbing ability of a host cell, which comprises introducing into a host cell an expression plasmid formed by combining (1) a promoter capable of functioning in a host cell, (2) a nicotianamine aminotransferase gene and (3) a terminator capable of functioning in a host cell, operably linked in the above described order and transforming said host cell,

(12) The process in accordance with the foregoing item 11, wherein the host cell is a plant cell,

(13) The process in accordance with the foregoing item 12, wherein the gene of the nicotianamine aminotransferase is the gene as defined in the foregoing item 2,

(14) A gene fragment having a partial sequence of the gene in accordance with the foregoing item 2, 3 or 4 (hereinafter, referred to as the gene fragment of the present invention),

(15) The gene fragment in accordance with the foregoing item 14, wherein the number of the base is 15 or more and 50 or less,

(16) The gene fragment in accordance with the foregoing item 14 having the nucleotide sequence represented by SEQ ID NO: 5 or 6,

(17) A process for detecting a nicotianamine aminotransferase gene, which comprises detecting from plant gene fragments a nicotianamine aminotransferase gene having a nucleotide sequence encoding an amino acid sequence of an enzyme with the nicotianamine aminotransferase activity or a gene fragment thereof by applying the hybridization method using the gene fragment in accordance with the foregoing item 14, 15 or 16 (hereinafter, referred to as the process for detection of the present invention),

(18) A process for amplifying a nicotianamine aminotransferase gene, which comprises amplifying a nicotianamine aminotransferase gene having a nucleotide sequence encoding an amino acid sequence of an enzyme with the nicotianamine aminotransferase activity or a gene fragment thereof by applying PCR (polymerase chain reaction) on a plant gene fragment using the gene fragment as defined in the foregoing item 14, 15 or 16 as a primer (hereinafter, referred to as the process for amplification of the present invention),

(19) A process for obtaining a nicotianamine aminotransferase gene, which comprises identifying a nicotianamine aminotransferase gene or a gene fragment thereof by the process as defined in the foregoing item 17 or 18, and isolating and purifying the identified gene or the gene fragment thereof, and

(20) A nicotianamine aminotransferase gene obtained by the process as defined in the foregoing item 19.

DETAILED DESCRIPTION OF THE INVENTION

The present invention will be described below in more detail.

The protein of the present invention comprises the amino acid sequence represented by SEQ ID NO: 2 or 4 or an amino acid sequence having said amino acid sequence with a single or plural amino acids deleted, replaced or added, and having the nicotianamine aminotransferase activity.

Such protein can be prepared from *Gramineae* plants, for example, barley (*Hordeum vulgare*) or the like by a process, for example, a process described below.

Examples of the protein of the present invention include an amino acid sequence of SEQ ID NO: 1 or 2 or an amino acid sequence having a molecular weight of 47 kDa comprising 429 amino acids beginning from the amino acid of NO: 33 in SEQ ID NO: 2.

The nicotianamine aminotransferase activity hereinafter refers to an ability of transferring an amino group from nicotianamine to 2-oxoglutarate.

The nicotianamine aminotransferase activity can be measured by, for example, a method described in Kanazawa, K et al., Journal of Experimental Botany, 45, 1903-1906 (1994) and others. Specifically, substrates nicotianamine, 2-oxoglutaric acid, and pyridoxal phosphate as a coenzyme are added to an enzyme solution and the mixture is reacted at 25° C. for 30 minutes. After the reaction, the reaction product is reduced by adding $NaBH_3$ and deoxymugineic acid is determined by HPLC.

In order to prepare the protein of the present invention from a Gramineae plant such as barley (*Hordeum vulgare*) or the like, for example, whole root of a Gramineae plant such as barley or the like treated for iron deficiency is triturated and the protein of the present invention is partly purified by subjecting the obtained extract to hydrophobic interaction chromatography, adsorption chromatography, anion exchange chromatography, gel filtration, and second adsorption chromatography in this order using the activity as an indicator. The individual protein fraction obtained from the second adsorption chromatography is subjected to two-dimensional electrophoresis and protein spots are detected which rises and falls in proportion to the intensity of nicotianamine aminotransferase activity of each fraction. The detected spots indicate the protein of the present invention. The protein of the present invention can be purified by isolating from the two-dimensional electrophoresis gel.

Mugineic acid analogues such as deoxymugineic acid produced by a reaction catalyzed by the protein of the present invention and a subsequent reduction reaction, mugineic acid and 3'-hydroxymugineic acid produced by a still subsequent hydroxylation reaction, or the like, solubilizes iron by forming a chelate complex with insoluble iron in the soil. Some kind of plants can biosynthesize said mugineic acid analogues, which are secreted from their root to the soil in the rooting zone, thereby solubilizing insoluble iron in the form of a mugineic acid complex and absorbing the iron complex directly through the root. Therefore, it is possible to enhance production of mugineic acid analogues and increase ability of absorbing insoluble iron by appropriately expressing a large amount of the protein of the present invention in said plants.

The gene of the present invention encodes a protein comprising the amino acid sequence represented by SEQ ID NO: 2 or 4 or an amino acid sequence having said amino acid sequence with a single or plural amino acids deleted, replaced or added, and having the nicotianamine aminotransferase activity.

Such gene can be prepared from Gramineae plants, for example, barley (*Hordeum vulgare*) or the like by a process, for example, a process described below.

Further, the gene of the present invention includes a gene encoding a protein comprising the amino acid sequence represented by SEQ ID NO: 2 or 4 or an amino acid sequence having said amino acid sequence with a single or plural amino acids deleted, replaced or added, and having the nicotianamine aminotransferase activity and encompasses a gene, for example, that hybridizes with the said gene sequence under stringent conditions. The stringent conditions herein refer to conditions used, for example, in the screening of cDNA library described in Example 4.

Specific examples of the nucleotide sequence of the gene include the nucleotide sequence represented by SEQ ID NO: 1 (the loci of CDS being 62-1444) or SEQ ID NO: 3 (the loci of CDS being 76-1731).

It is possible to increase ability of absorbing insoluble iron in the soil in the rooting zone and improve resistance to iron deficiency by introducing the gene of the present invention into a plant which absorbs iron making use of mugineic acid compounds thereby enhancing biosynthesizing ability of mugineic acid compounds in the obtained transformant plant.

In order to prepare the gene of the present invention, for example, the amino acid sequence of peptide fragments obtained by partially hydrolyzing the protein of the present invention and the N-terminal amino acid sequence of the protein of the present invention are determined by a protein sequencer. Two or more primers comprising DNA sequences expected from these amino acid sequences are synthesized. By conducting PCR using as a template a cDNA synthesized from mRNA prepared from the root of a Gramineae plant such as barley treated for iron deficiency by means of a reverse transcriptase, cDNA fragment of the gene of the present invention is amplified. Using the amplified cDNA fragment as a probe, screening of cDNA library described below is performed. A cDNA is synthesized from mRNA prepared from the root of a Gramineae plant such as barley treated for iron deficiency by means of a reverse transcriptase and this is integrated into a phage vector such as lambda ZAPII or the like or a plasmid vector such as pUC or the like to prepare a cDNA library. This library is screened using the above-mentioned probe and a cDNA of the nicotianamine aminotransferase gene is selected. The selected cDNA can be confirmed to be that of the nicotianamine aminotransferase gene (cDNA of the gene of the present invention) by determining the sequence of the selected cDNA.

In order to obtain genome DNA using the cDNA selected in this manner and determine its sequence, for example, plant tissue such as leaf, stem, root or the like is instantly frozen and sufficiently triturated with a mortar and pestle or a Waring blender. The genome DNA is extracted from the obtained triturated product according to the ordinary method as described in Itaru Watanabe (supervisor), Masahiro Sugiura (editor), "Cloning and Sequencing (a manual for experiment of plant biotechnology)", Nosonbunka-sha, Tokyo (1989) or the like. The obtained genome DNA is digested with an appropriate restriction enzyme and the obtained genome DNA fragments are fractionated by a known method such as sucrose density gradient centrifugation or cesium chloride equilibrium centrifugation or the like. Each of the genome DNA fragment fractions is subjected to normal Southern hybridization using the selected cDNA (cDNA of the gene of the present invention) as a probe to decide a genome DNA fragment fraction containing the desired gene.

A genome DNA library is prepared by ligating the genome DNA fragment fraction to a commercially available vector such as plasmid, phage, cosmid or the like. The library is subjected to normal screening by hybridization using the cDNA of the gene of the present invention as a probe to obtain a genome DNA clone containing a nucleotide sequence encoding the amino acid sequence of the protein of the present invention. The obtained DNA clone can be subcloned to a vector, for example, plasmid or the like suitable for analysis of gene sequence and the sequence is analyzed according to a routine method to determine the sequence of the genome DNA containing a sequence encoding the amino acid sequence of the protein of the present invention.

The transcription initiation site of genome DNA of the gene of the present invention can be determined by the primer extension method described in Bina-Stem, Met et al., Proc. Natl. Acad. Sci. USA, 76, 731 (1979), Sollner-Webb and Reeder, R. H., Cell, 18, 485 (1979) or the like or the S1 mapping method described in Berk, A. J. and Sharp, P. A., Proc. Natl. Acad. Sci. USA, 75, 1274 (1978). A TATA sequence necessary for the transcription initiation is present in the upstream of the transcription initiation site decided in this manner. A promoter sequence bearing control of gene expression is present usually at 1 kb to about 10 kb upstream of this transcription initiation site. The promoter region of the gene of the present invention can be finally determined, for example, by connecting gene fragments having promoter regions of various length with a reporter gene such as GUS or the like, preparing transgenic plants into which the connected product are introduced, and studying presence or absence of expression of the reporter gene in various tissues of the prepared plants.

On the other hand, a terminator sequence is present in the genome DNA region corresponding to a poly-A sequence usually present in the downstream of a poly (A) addition signal (consensus sequence being AATAAA) which exists in a terminal 3'-nontranslation region at the downstream of termination codon, and has an effective translation terminating function.

The plasmid of the present invention contains a gene encoding a protein comprising the amino acid sequence represented by SEQ ID NO: 2 or 4 or an amino acid sequence having said amino acid sequence with a single or plural amino acids deleted, replaced or added, and having the nicotianamine aminotransferase activity.

Preferred specific examples of the plasmid include a plasmid prepared by cloning a nicotianamine aminotransferase gene having a nucleotide sequence encoding the amino acid sequence represented by SEQ ID NO: 1 into pSK-(Strategene). This has a characteristic that its vector portion is small, it has a great number of copies in *Escherichia coli*, and thus it is suitable for preparation of DNA or analysis of DNA structure.

The expression plasmid of the present invention can be constructed by combining (1) a promoter capable of functioning in a host cell, (2) the gene encoding a protein comprising the amino acid sequence represented by SEQ ID NO: 2 or 4 or an amino acid sequence having said amino acid sequence with a single or plural amino acids deleted, replaced or added, and having the nicotianamine aminotransferase activity and (3) a terminator capable of functioning in a host cell, operably linked in the above described order.

The expression "operably linked" used hereinafter means that, when the constructed plasmid is introduced into a host cell to transform it, the gene of the present invention is integrated under the control of a promoter such that the gene has a function of expressing the protein of the present invention in said host cell.

The promoter capable of functioning in a host cell includes, for example, *Escherichia coli* lactose operon promoter, yeast alcohol dehydrogenase (ADH) promoter, adenovirus major late (Ad. ML) promoter, SV40 early promoter, baculovirus promoter and the like. When the host cell is a plant cell, the promoter includes, for example, T-DNA derived constitutive promoters such as nopaline synthase gene (NOS) promoter, octopine synthase gene (OCS) promoter and the like, plant virus derived promoters such as cauliflower mosaic virus (CaMV) derived 19S and 35S promoters and the like, and inducible promoters such as phenylalanine ammonialyase (PAL) gene promoter, chalcone synthase (CHS) gene promoter, pathogen-related (PR) gene promoter and the like. Further, it includes known plant promoters not limited to them.

The terminator capable of functioning in a host cell includes, for example, yeast HIS terminator sequence, ADH1 terminator, SV40 early splicing region and the like. When the host cell is a plant cell, the terminator includes, for example, T-DNA derived constitutive terminators such as nopaline synthase gene (NOS) terminator and the like, plant virus derived terminators such as garlic virus GV1, GV2 terminators and the like. Further, it includes known plant terminators not limited to them.

A host cell is transformed by introducing such plasmid ((expression) plasmid of the present invention) into said host cell. When the host cell is a plant cell, the (expression) plasmid of the present invention is introduced into a plant cell by any of conventional means such as *Agrobacterium* infection method (JP-B-2-58917 and JP-A-60-70080), electroporation method into protoplast (JP-A-60-251887 and JP-A-5-68575), particlegunmethod (JP-A-508316and JP-A-63-258525) and the like, and a transformed plant cell can be obtained by selecting a plant cell into which the gene of the present invention is introduced. The transformed plant body is obtained by regenerating a plant body according to a conventional plant cell culturing process, for example, described in Hirohumi Utimiya, Manual for Plant Gene Manipulation (Method for Producing Transgenic Plants), Published by Kodansha Scientific (ISBN4-06-153515-7C3045), 1990, pages 27-55.

By introducing the plasmid of the present invention into host cells which are any kind of microorganism such as *Escherichia coli* or the like and allowing high expression in said host cells, a large amount of the protein of the present invention can easily be isolated from the host cells. A screening system for inhibitors to nicotianamine aminotransferase activity constructed by utilizing the mass produced protein of the present invention. For example, according to the process for measuring nicotianamine aminotransferase activity described above, substrates nicotianamine, 2-oxoglutaric acid and pyridoxal phosphate as the coenzyme as well as a candidate inhibitor compound are added to the prepared enzyme solution, and the mixture is reacted at 25° C. for 30 minutes. After the reaction, compounds showing no nicotianamine aminotransferase activity are selected by reducing the reaction product with addition of NaBH$_3$ and deoxymugineic acid by HPLC.

In plants absorbing iron utilizing mugineic acid compounds, expression of the nicotianamine aminotransferase gene is strongly induced in iron deficiency conditions. Since the common soil (upland soil) is under the oxidative conditions and the ferric iron concentration in soil solution is only a level extremely lower than $10^{-4}$-$10^{-8}$ M that is required by plants, nicotianamine aminotransferase gene and mugineic acid biosynthesis gene are always strongly induced. In other words, plants positively absorb insoluble iron by routinely biosynthesizing mugineic acid compounds and secreting them from the root to the soil in the rooting zone.

The inhibitors to nicotianamine aminotransferase activity selected by the screening system may be compounds useful as selective herbicides against plants that absorb iron by utilizing compounds analogous to mugineic acid.

Further, the present invention provides a process for enhancing iron absorbing ability, which comprises introducing in a host cell an expression plasmid formed by combining (1) a promoter capable of functioning in a host cell, (2) a nicotianamine aminotransferase gene and (3) a terminator capable of functioning in a host cell, operably in the above described order and transforming said host cell. The promoter capable of functioning in a host cell includes the promoters as described above.

The nicotianamine aminotransferase gene includes, for example, a plant derived nicotianamine aminotransferase gene and preferably the gene of the present invention.

The terminator capable of functioning in a host cell includes the terminators as described above.

The gene fragment of the present invention refers to a gene fragment having a partial sequence of the gene of the present invention represented by SEQ ID NO: 1 or 3 and includes a gene fragment having a partial sequence of the gene encoding a protein comprising the amino acid sequence represented by SEQ ID NO: 2 or 4 or an amino acid sequence having said amino acid sequence with a single or plural amino acids deleted, replaced or added, and having the nicotianamine aminotransferase activity, specifically, for example, a gene fragment represented by SEQ ID NO: 5 or 6.

These gene fragments are useful as probes in hybridization or primers in PCR. Particularly, as primers used in PCR, a gene fragment having 15 or more and 50 or less nucleotides are preferred.

The process for detection of the present invention is a process in which a nicotianamine aminotransferase gene having a nucleotide sequence encoding an amino acid sequence of an enzyme with the nicotianamine aminotransferase activity or a gene fragment thereof is detected from plant gene fragments by applying the hybridization method using the gene fragment of the present invention as a probe.

Specifically, for example, the process can be performed according to the method described in "Molecular Cloning: A Laboratory Manual, 2nd edition" (1989), Cold Spring Harbor Laboratory Press or in "Current Protocols in Molecular Biology" (1987), John Wiley & Sons, Inc., ISBN0-471-50338-X. The gene fragments used here may include, for example, cDNA library, genome DNA library or the like of the targeted plant. Said plant gene fragments may be a commercially available library as such derived from a plant, or may also be a library prepared according to the conventional method for preparing a library described in "Molecular Cloning: A Laboratory Manual, 2nd edition" (1989), Cold Spring Harbor Laboratory Press or in "Current Protocols in Molecular Biology" (1987), John Wiley & Sons, Inc., ISBN0-471-50338-X.

It can also be possible to obtain nicotianamine aminotransferase gene by identifying the nicotianamine aminotransferase gene or a fragment thereof according to the process for detection of the present invention and isolating/purifying the identified gene or gene fragment.

The process for detection of the present invention may be utilized in analysis of plants. Specifically, a plant genome DNA is prepared from different cultivars of a specific plant species according to the process for detection of the present invention the ordinary method described in Itaru Watanabe (supervisor), Masahiro Sugiura (editor), "Cloning and Sequencing (a manual for experiment of plant biotechnology)", Nosonbunka-sha, Tokyo (1989) or the like. It is then incised with at least several kinds of suitable restriction enzymes, electrophoresed, and used for preparing a filter by brotting according to the ordinary method.

Hybridization is conducted on the filter using a probe prepared by the ordinary method and differences in phenotype character accompanied by mugineic acid biosynthesis between cultivars based on the difference in length of DNA fragments. Further, a plant is decided to be a recombinant gene plant if the plant has a greater number of detected hybridization bands than a non-recombinant gene plant when the specific plant is compared with the non-recombinant plant. This method is preferably carried out according to the RFLP (Restriction Fragment Length Polymorphism) method described in Ko Shimamoto and Takuji Sasaki (supervisors), "Protocols for PCR Experiment on Plants", Shujunsha, Tokyo (1995), ISBN4-87962-144-7, pp 90-94.

The process for amplification of the present invention is a process in which a nicotianamine aminotransferase gene having a nucleotide sequence encoding an amino acid sequence of an enzyme with the nicotianamine aminotransferase activity or a gene fragment thereof is amplified by applying PCR (polymerase chain reaction) on a plant gene fragments using the gene fragment of the present invention as a primer. Specifically, for example, the process can be performed according to the method described in Ko Shimamoto and Takuji Sasaki (supervisors), "Protocols for PCR Experiment on Plants", Shujunsha, Tokyo (1995), ISBN4-87962-144-7 or the like.

It can also be possible to obtain nicotianamine aminotransferase gene by identifying the nicotianamine aminotransferase gene or a fragment thereof according to the process for amplification of the present invention and isolating/purifying the identified gene or gene fragment.

Further, the process for amplification of the present invention may be utilized in analysis of plants. Specifically, for example, a part or the whole of the gene of the present invention is amplified by conducting PCR using a plant genome DNA prepared from a specific plant species as a template and the gene fragment of the present invention as a primer. The obtained PCR product is mixed with a formaldehyde solution and the mixture is denatured by heating at 85° C. for 5 minutes, followed by rapid cooling on ice. This sample is electrophoresed on, for example, 6% acrylamide gel containing glycerol at a concentration of 0% or 10%. The electrophoresis is carried out with a commercially available electrophoresis apparatus for SSCP (Single Strand Conformation Polymorphism) keeping the gel temperature at, for example, 5° C., 25° C., 37° C. and so on. The migrated gel is subjected to ethidium bromide staining or the like using a commercially available reagent to detect DNA.

Differences in phenotype character accompanied by mugineic acid biosynthesis between cultivars based on mutation in the gene of the present invention is analyzed from the differences immigration of the DNA fragments detected. This method is preferably carried out according to the method described in Ko Shimamoto and Takuji Sasaki (supervisors), "Protocols for PCR Experiment on Plants", Shujunsha, Tokyo (1995), ISBN4-87962-144-7, pp 141-146.

EXAMPLES

The present invention will now be described in more detail on the bases of Examples, which should not be construed as a limitation upon the scope of the present invention.

Example 1

Method of Isolating the Protein of the Present Invention

In an extraction buffer solution (0.2 M Tris-HCl, 10 mM EDTA, 0.1 mM p-APMSF, 10 mM DTT, 5% glycerol, 5% polyvinyl pyrrolidone, pH 8.) was triturated 150 g of root of barley treated for iron deficiency. The trituration product was centrifuged at 8,000×g for 30 minutes and the supernatant was separated. Ammonium sulfate was added to the obtained supernatant until 30% saturation was attained. The produced sample was applied over Butyl Toyopearl (manufactured by Toso) equilibrated with 30% saturated ammonium sulfate buffer (50 mM Tris-HCl (pH 8.0), 5 mM EDTA, 10 mM DTT), and eluted with 15% saturated ammonium sulfate buffer after washing with the former buffer. To eluted fractions was added p-APMSF at a final concentration of 0.1 mM and the mixture was dialyzed overnight against 0.1 mM KCl, 50 mM $KH_2PO_4/K_2HPO_4$ (pH 6.8), 10 mM DTT, followed by application over Hydroxylapatite (100-350 mesh, manufactured by Nakarai) equilibrated with said buffer. Then it was washed with the same buffer and eluted with 0.5 M $KH_2PO_4/K_2HPO_4$ (pH 6.8), 10 mM DTT. The eluted fractions were treated with Molecut (Millipore, differential molecular weight 10,000) in order to exchange buffer with 20 mM Tris-HCl (pH 8.0), 10 mM KCl, 10 mM DTT and applied over DEAE Sephasel (manufactured by Pharmacia) equilibrated with the same buffer. After washing with the same buffer, it was eluted with 10 mM-500 mM KCl concentration gradient. Non-adsorbed fractions from DEAE Sephasel were treated with Molcut in order to exchange buffer with 20 mM Tris-HCl (pH 8.0), 10 mM KCl, 5 mM EDTA, 1 mM DTT and applied over NA-Sepharose 4B which was EAH-Sepharose 4B (manufactured by Pharmacia) having bound nicotianamine (NA). After washing with the same buffer, it was eluted with 1 mM NA, 10 mM KCl, 20 mM Tris-HCl (pH 6.0). The eluted fractions were subjected to two-dimensional electrophoresis, which allowed very concentrated spot as compared with the sample before applying on NA-Sepharose 4B column. The spot indicated the protein of the present invention, which was isolated by separating said spot.

The N-terminal amino acid sequence of the protein of the present invention as separated was analyzed by a protein sequencer (manufactured by Applied Biosystems). The result showed revealed an amino acid sequence shown by the amino acids of Nos 33 to 47 in the Seq. ID NO. 1. Further, N-terminal amino acid sequences for 3 peptide fragments formed by treating it with 70% formic acid solution containing 1% bromocyan were analyzed in the same manner.

Example 2

Preparation of a Probe for Cloning of cDNA of the Protein of the Present Invention From 6 g of root of barley treated for iron deficiency 255 μg of whole RNA was recovered according to the SDS-phenol method described in Itaru Watanabe (supervisor), Masahiro Sugiura (editor), "Cloning and Sequencing (a manual for experiment of plant biotechnology)", Noson-bunka-sha, Tokyo (1989), pp 34-40. From the recovered whole RNA, 75 μg portion was taken and used to prepare poly (A) +RNA using Dynabeads mRNA Purification Kit (manufactured by Dynal). The prepared poly (A) +RNA was reverse transcribed with dT17 adapter primer (5'-GACTC-GAGTCGACATCGATTTTTTTTTTTTTTTT-3') (SEQ ID NO:7) to prepare cDNA. A part of the prepared cDNA was used for amplification of cDNA fragment of the gene of the present invention by two steps PCR. In the first reaction, PCR was conducted with a primer 1 (5'-GCIGTIGARTG-GAAYTTYGCIMG-3') (SEQ ID NO:5) synthesized on the basis of N-terminal amino acid sequence of the protein of the present invention and the above described dT17 adapter primer and using the obtained cDNA as a template at 94° C. (40 seconds), 40° C. (1 minute), and 72° C. (2 minutes), repeated by 25 cycles, and at 94° C. (40 seconds), 45° C. (1 minute), and 72° C. (2 minutes), repeated by 25 cycles. Using this PCR reaction solution as a template, the second PCR was conducted with a primer 2 (5'-GCDATRTGIC-CRAAIACICC-3') (SEQ ID NO:6) synthesized on the basis of N-terminal amino acid sequence of the peptide fragment formed by treating with 70% formic acid solution containing 1% bromocyan as described above and the primer 1 at 94° C. (40 seconds), 45° C. (1 minute), and 72° C. (2 minutes), repeated by 40 cycles. The DNA fragment of about 600 bp amplified by the second PCR was purified by excising from 0.8% agarose electrophoresis gel and used as a probe for screening cDNA library.

Example 3

Preparation of cDNA Library from Root of Barley Treated for Iron Deficiency

Using a commercially available cDNA synthesis kit (Super Script (trademark) Plasmid System for cDNA Synthesis and Plasmid Cloning, manufactured by Gibco BRL), cDNA was synthesized from 5 μg of poly (A) +RNA prepared from root of barley treated for iron deficiency described in Example 2. The product was ligated with SalI adapter and incised with NotI to recover cDNA.

A vector for cDNA library (hereinafter, referred to as pYH23) was prepared by adding some modification to yeast multi-copy plasmid YEplac181 described in R. Daniel Gietz and Akio Sugino, Gene, 74 (1988), pp 527-534. Specifically, HindIII and BamHI to EcoRI site in the multi-cloning site of YEplac181 was eliminated. Further, promoter and terminator sequences of alcohol dehydrogenase derived from pTV-100 were subcloned at SphI site, and NotI linker was inserted at BamHI site of this fragment.

The pYH23 prepared in this manner was digested with NotI and XhoI, after inserting cDNA prepared as above,

*Escherichia coli* XL1-Blue strain was transformed to provide cDNA library derived from 300,000 independent colonies.

Example 4

Screening of cDNA Clones of the Present Invention

A probe DNA for cDNA cloning of the protein of the present invention was prepared by radioactively labeling the probe prepared in Example 3 with a commercially obtainable radioactivity label kit (Random Primer DNA Labeling Kit Ver. 2, TaKaRa). *Escherichia coli* having a plasmid DNA of cDNA library derived from root of barley treated for iron deficiency as prepared in Example 3 was inoculated in LB medium, incubated at 37° C. for 10 hours, and then transferred to a commercially available Nylon membrane (Hybond (trademark)–N+, Amersham Life Science). The membrane was treated with 10% SDS for 3 minutes, an alkaline denaturation solution (0.5 M NaOH, 1.5 M NaCl) for 5 minutes, a neutralizing solution (0.5 M Tris-HCl (pH 7.0), 1.5 M NaCl) for 3 minutes, 2×SSPE (20 mM phosphate buffer (pH 7.4), 0.3 M NaCl, 5 mM EDTA) twice for 3 minutes, dried, and irradiated with ultraviolet rays for 3 minutes to irreversibly fix DNA on the membrane. Prehybridization was carried out at 65° C. for 1 hour using a prehybridization solution (5× Denhart's solution, 5×SSPE, 0.1% SDS, 100 µg/ml denatured salmon test is DNA). Then, hybridization was carried out in a solution having the radioactively labeled probe added to a hybridization solution (5× Denhart's solution, 5×SSPE, 0.1% SDS) at 65° C. for 12 hours. Thereafter, the membrane was washed once with 6×SSP at 65° C. for 10 minutes, twice with 2×SSP, 0.1% SDS at 42° C. for 10 minutes, and exposed to Fuji Medical X-ray Film to detect positive colonies. Second and third screenings were performed in the same manner and cDNA clone of the protein of the present invention was isolated.

Example 5

Determination of Nuceotide Sequence of cDNA Encoding the Protein of the Present Invention The cDNA clone of the protein of the present invention isolated in Example 4 was subcloned in a plasmid vector pBluescript SK(-) according to the conventional method described in J. Sambrook, E. F. Fritsh, T. Maniatis, "Molecular Cloning, Second Edition" Cold Spring Harbor Press (1989) to give a plasmid cDNA clone. Nucleotide sequence (SEQ. ID NO. 1 or 3) of the insert in said cDNA clone was determined (1) by 373A DNA Sequencer manufactured by Applied Biosystems using Taq Dye Primer Cycle Sequencing Kit (manufactured by Applied Biosystems), (2) by DSQ-1000L DNA Sequencer (manufactured by Shimadzu) using Thermo Sequence Fluorescent Labeled Primer Cycle Sequencing Kit (manufactured by Amersham Life Science), or (3) by BAS-2000 (manufactured by Fuji Film) using BcaBEST (trademark) Dideoxy Sequencing Kit (manufactured by TaKaRa). The total amino acid sequences of the protein (see SEQ ID NO: 2 and 4) were determined from the sequence (see SEQ ID NO: 1 and 3). The protein of the SEQ ID NO: 2 had 461 amino acids and its molecular weight was calculated to be 49564.15, and the protein of the SEQ ID NO: 4 had 551 amino acids and its molecular weight was calculated to be 58148.62, According to the present invention, it could be possible to provide a novel nicotianamine aminotransferase, a gene therefor and so on.

---

What is claimed is:

1. An isolated protein comprising:
   (a) the amino acid sequence of SEQ ID NO: 2 or 4;
   (b) an amino acid sequence encoded by a nucleotide sequence which comprises a DNA sequence that is amplifiable from Gramineae plant cDNA by polymerase chain reaction with the primers of SEQ ID NOs:5 and 6 repeating a cycle of incubation at 94° C. for 40 seconds, followed by 40° C. for 1 minute, and followed by 72° C. for 2 minutes, 25 times, and then repeating a cycle of incubation at 94° C. for 40 seconds, followed by 45° C. for 1 minute, and followed by 72° C. for 2 minutes, 25 times, wherein said amino acid sequence has nicotianamine aminotransferase activity; or
   (c) an amino acid sequence encoded by a nucleotide sequence from barley, wherein said nucleotide sequence hybridizes to the nucleotide sequence of SEQ ID NO: 1 or 3 when incubated in a solution of 5× Denhart's solution, 5×SSPE and 0.1% SDS at 65° C. for 12 hours, washed once with 6×SSPE at 65° C. for 10 minutes and washed twice with 2×SSPE, 0.1% SDS at 42° C. for 10 minutes, and wherein said amino acid sequence has nicotianamine aminotransferase activity.

2. An isolated protein comprising the amino acid sequence of SEQ ID NO: 2 or 4.

3. The isolated protein as defined in claim 1, wherein said protein consists of the amino acid sequence of SEQ ID NO: 2 or 4.

4. The isolated protein as defined in claim 1, comprising:
   (b) an amino acid sequence encoded by a nucleotide sequence with comprises a DNA sequence that is amplifiable from Gramineae plant cDNA by polymerase chain reaction with the primers of SEQ ID NOs:5 and 6 repeating a cycle of incubation at 94° C. for 40 seconds, followed by 40° C. for 1 minute, and followed by 72° C. for 2 minutes, 25 times, and then repeating a cycle of incubation at 94° C. for 40 seconds, followed by 45° C. for 1 minute, and followed by 72° C. for 2 minutes, 25 times, wherein said amino acid sequence has nicotianamine aminotransferase activity.

5. The isolated protein as defined in claim 1, comprising:
   (c) an amino acid sequence encoded by a nucleotide sequence from barley, wherein said nucleotide sequence hybridizes to the nucleotide sequence of SEQ ID NO: 1 or 3 when incubated in a solution of 5× Denhart's solution, 5×SSPE and 0.1% SDS at 65° C. for 12 hours, washed once with 6×SSPE at 65° C. for 10 minutes and washed twice with 2×SSPE, 0.1% SDS at 42° C. for 10 minutes, and wherein said amino acid sequence has nicotianamine aminotransferase activity.

* * * * *

SEQUENCE LISTING

<160> NUMBER OF SEQ ID NOS: 7

<210> SEQ ID NO 1
<211> LENGTH: 1660
<212> TYPE: DNA
<213> ORGANISM: Hordeum vulgare
<220> FEATURE:
<221> NAME/KEY: CDS
<222> LOCATION: (62)..(1444)

<400> SEQUENCE: 1

```
attgactagc tagttcattc cctgccacac tgctagtact cctcctcgtt tcctcgtggc      60 a atg gta cac cag agc aac ggc cac ggc gag gcc gcc gcc gcc gcc gcc    109
  Met Val His Gln Ser Asn Gly His Gly Glu Ala Ala Ala Ala Ala Ala
  1               5                  10                  15 aac ggc aag agc aac ggg cac gcc gcc gcc gcg aac ggc aag agc aac    157
Asn Gly Lys Ser Asn Gly His Ala Ala Ala Ala Asn Gly Lys Ser Asn
             20                  25                  30 ggg cac gcg gcg gcg gcg gcg gtg gag tgg aat ttc gcc cgg ggc aag    205
Gly His Ala Ala Ala Ala Ala Val Glu Trp Asn Phe Ala Arg Gly Lys
         35                  40                  45 gac ggc atc ctg gcg acg acg ggg gcg aag aac agc atc cgg gcg ata    253
Asp Gly Ile Leu Ala Thr Thr Gly Ala Lys Asn Ser Ile Arg Ala Ile
     50                  55                  60 cgg tac aag atc agc gcg agc gtg gag gag agc ggg ccg cgg ccc gtg    301
Arg Tyr Lys Ile Ser Ala Ser Val Glu Glu Ser Gly Pro Arg Pro Val
 65                  70                  75                  80
```

-continued

| | |
|---|---|
| ctg ccg ctg gcc cac ggt gac ccg tcc gtg ttc ccg gcc ttc cgc acg<br>Leu Pro Leu Ala His Gly Asp Pro Ser Val Phe Pro Ala Phe Arg Thr<br>        85         90        95 | 349 |
| gcc gtc gag gcc gaa gac gcc gtc gcc gcc gcg ctg cgc acc ggc cag<br>Ala Val Glu Ala Glu Asp Ala Val Ala Ala Ala Leu Arg Thr Gly Gln<br>       100         105        110 | 397 |
| ttc aac tgc tac gcc gcc ggc gtc ggc ctc ccc gcc gca cga agc gcc<br>Phe Asn Cys Tyr Ala Ala Gly Val Gly Leu Pro Ala Ala Arg Ser Ala<br>      115         120        125 | 445 |
| gta gca gag cac ttg tca cag ggc gtg ccc tac aag cta tcg gcc gac<br>Val Ala Glu His Leu Ser Gln Gly Val Pro Tyr Lys Leu Ser Ala Asp<br> 130         135        140 | 493 |
| gac gtc ttc ctc acc gcc ggc gga act cag gcg atc gaa gtc ata atc<br>Asp Val Phe Leu Thr Ala Gly Gly Thr Gln Ala Ile Glu Val Ile Ile<br>145         150        155        160 | 541 |
| ccg gtg ctg gcc cag act gcc ggc gcc aac ata ctg ctt ccc cgg cca<br>Pro Val Leu Ala Gln Thr Ala Gly Ala Asn Ile Leu Leu Pro Arg Pro<br>       165         170        175 | 589 |
| ggc tat cca aat tac gag gcg cga gcg gca ttc aac aag ctg gag gtc<br>Gly Tyr Pro Asn Tyr Glu Ala Arg Ala Ala Phe Asn Lys Leu Glu Val<br>      180         185        190 | 637 |
| cgg cac ttc gac ctc atc ccc gac aag ggg tgg gag atc gac atc gac<br>Arg His Phe Asp Leu Ile Pro Asp Lys Gly Trp Glu Ile Asp Ile Asp<br>        195         200        205 | 685 |
| tcg ctg gaa tcc atc gcc gac aag aac acc acc gcg atg gtc atc ata<br>Ser Leu Glu Ser Ile Ala Asp Lys Asn Thr Thr Ala Met Val Ile Ile<br>210         215        220 | 733 |
| aac cca aac aat ccg tgc ggc agc gtt tac tcc tac gac cat ctg gcc<br>Asn Pro Asn Asn Pro Cys Gly Ser Val Tyr Ser Tyr Asp His Leu Ala<br>225         230        235        240 | 781 |
| aag gtc gcg gag gtg gca agg aag ctc gga ata ttg gtg atc gct gac<br>Lys Val Ala Glu Val Ala Arg Lys Leu Gly Ile Leu Val Ile Ala Asp<br>        245         250        255 | 829 |
| gag gtt tac ggc aaa ctg gtt ctg ggc agc gcc ccg ttt atc ccg atg<br>Glu Val Tyr Gly Lys Leu Val Leu Gly Ser Ala Pro Phe Ile Pro Met<br>      260         265        270 | 877 |
| ggc gtc ttt ggg cac att gcc ccg gtc ttg tcc att gga tct ctg tcc<br>Gly Val Phe Gly His Ile Ala Pro Val Leu Ser Ile Gly Ser Leu Ser<br>        275         280        285 | 925 |
| aag tcg tgg ata gtg cct gga tgg cga ctt gga tgg gtg gcg gtg tac<br>Lys Ser Trp Ile Val Pro Gly Trp Arg Leu Gly Trp Val Ala Val Tyr<br> 290         295        300 | 973 |
| gac ccc aca aag att tta gag aaa act aag atc tct acg tct att acg<br>Asp Pro Thr Lys Ile Leu Glu Lys Thr Lys Ile Ser Thr Ser Ile Thr<br>305         310        315        320 | 1021 |
| aat tac ctt aat gtc tca acg gac cca gca acc ttc gtt cag gaa gct<br>Asn Tyr Leu Asn Val Ser Thr Asp Pro Ala Thr Phe Val Gln Glu Ala<br>        325         330        335 | 1069 |
| ctt cct aaa att ctt gag aac aca aaa gca gat ttc ttt aag agg att<br>Leu Pro Lys Ile Leu Glu Asn Thr Lys Ala Asp Phe Phe Lys Arg Ile<br>      340         345        350 | 1117 |
| att ggt cta cta aag gaa tca tca gag ata tgt tat agg gaa ata aag<br>Ile Gly Leu Leu Lys Glu Ser Ser Glu Ile Cys Tyr Arg Glu Ile Lys<br>      355         360        365 | 1165 |
| gaa aac aaa tat att acg tgt cct cac aag cca gaa gga tcg atg ttt<br>Glu Asn Lys Tyr Ile Thr Cys Pro His Lys Pro Glu Gly Ser Met Phe<br>370         375        380 | 1213 |
| gta atg gtc aaa cta aac tta cat ctt ttg gag gag atc cat gac gac<br>Val Met Val Lys Leu Asn Leu His Leu Leu Glu Glu Ile His Asp Asp | 1261 |

```
                385              390              395              400
ata gat ttt tgc tgc aag ctc gca aag gaa gaa tca gta att tta tgt      1309
Ile Asp Phe Cys Cys Lys Leu Ala Lys Glu Glu Ser Val Ile Leu Cys
                    405              410              415 cca ggg agt gtt ctt gga atg gaa aat tgg gtc cgt att act ttt gcc      1357
Pro Gly Ser Val Leu Gly Met Glu Asn Trp Val Arg Ile Thr Phe Ala
            420              425              430 tgc gtt cca tct tct ctt caa gat gga ctc gaa agg gtc aaa tca ttc      1405
Cys Val Pro Ser Ser Leu Gln Asp Gly Leu Glu Arg Val Lys Ser Phe
        435              440              445 tgt caa agg aac aag aag aag aat tct ata aat ggt tgt tagttgtaca       1454
Cys Gln Arg Asn Lys Lys Lys Asn Ser Ile Asn Gly Cys
    450              455              460 cacccctagt tgtacatctg actgaagctg taaatcattt ctagttatcc cccatttata    1514
tatttcaata aaacatattg taatggttct gttgtagctg tccaagtcat gtactctact    1574
ttttgatgta tttggcctca ttgccttgca tcaatttcaa taaaaatggt tgtgtacacc    1634
aaaaaaaaaa aaaaaaaaa aaaaa                                           1660

<210> SEQ ID NO 2
<211> LENGTH: 461
<212> TYPE: PRT
<213> ORGANISM: Hordeum vulgare

<400> SEQUENCE: 2

Met Val His Gln Ser Asn Gly His Gly Glu Ala Ala Ala Ala Ala Ala
 1               5                  10                  15

Asn Gly Lys Ser Asn Gly His Ala Ala Ala Asn Gly Lys Ser Asn
             20                  25                  30

Gly His Ala Ala Ala Ala Val Glu Trp Asn Phe Ala Arg Gly Lys
         35                  40                  45

Asp Gly Ile Leu Ala Thr Thr Gly Ala Lys Asn Ser Ile Arg Ala Ile
     50                  55                  60

Arg Tyr Lys Ile Ser Ala Ser Val Glu Glu Ser Gly Pro Arg Pro Val
 65                  70                  75                  80

Leu Pro Leu Ala His Gly Asp Pro Ser Val Phe Pro Ala Phe Arg Thr
                 85                  90                  95

Ala Val Glu Ala Glu Asp Ala Val Ala Ala Leu Arg Thr Gly Gln
            100                 105                 110

Phe Asn Cys Tyr Ala Ala Gly Val Gly Leu Pro Ala Ala Arg Ser Ala
        115                 120                 125

Val Ala Glu His Leu Ser Gln Gly Val Pro Tyr Lys Leu Ser Ala Asp
    130                 135                 140

Asp Val Phe Leu Thr Ala Gly Gly Thr Gln Ala Ile Glu Val Ile Ile
145                 150                 155                 160

Pro Val Leu Ala Gln Thr Ala Gly Ala Asn Ile Leu Leu Pro Arg Pro
                165                 170                 175

Gly Tyr Pro Asn Tyr Glu Ala Arg Ala Ala Phe Asn Lys Leu Glu Val
            180                 185                 190

Arg His Phe Asp Leu Ile Pro Asp Lys Gly Trp Glu Ile Asp Ile Asp
        195                 200                 205

Ser Leu Glu Ser Ile Ala Asp Lys Asn Thr Thr Ala Met Val Ile Ile
    210                 215                 220

Asn Pro Asn Asn Pro Cys Gly Ser Val Tyr Ser Tyr Asp His Leu Ala
225                 230                 235                 240
```

```
Lys Val Ala Glu Val Ala Arg Lys Leu Gly Ile Leu Val Ile Ala Asp
                245                 250                 255
Glu Val Tyr Gly Lys Leu Val Leu Gly Ser Ala Pro Phe Ile Pro Met
            260                 265                 270
Gly Val Phe Gly His Ile Ala Pro Val Leu Ser Ile Gly Ser Leu Ser
        275                 280                 285
Lys Ser Trp Ile Val Pro Gly Trp Arg Leu Gly Trp Val Ala Val Tyr
    290                 295                 300
Asp Pro Thr Lys Ile Leu Glu Lys Thr Lys Ile Ser Thr Ser Ile Thr
305                 310                 315                 320
Asn Tyr Leu Asn Val Ser Thr Asp Pro Ala Thr Phe Val Gln Glu Ala
                325                 330                 335
Leu Pro Lys Ile Leu Glu Asn Thr Lys Ala Asp Phe Phe Lys Arg Ile
            340                 345                 350
Ile Gly Leu Leu Lys Glu Ser Ser Glu Ile Cys Tyr Arg Glu Ile Lys
        355                 360                 365
Glu Asn Lys Tyr Ile Thr Cys Pro His Lys Pro Gly Ser Met Phe
    370                 375                 380
Val Met Val Lys Leu Asn Leu His Leu Leu Glu Ile His Asp Asp
385                 390                 395                 400
Ile Asp Phe Cys Cys Lys Leu Ala Lys Glu Glu Ser Val Ile Leu Cys
                405                 410                 415
Pro Gly Ser Val Leu Gly Met Glu Asn Trp Val Arg Ile Thr Phe Ala
            420                 425                 430
Cys Val Pro Ser Ser Leu Gln Asp Gly Leu Glu Arg Val Lys Ser Phe
        435                 440                 445
Cys Gln Arg Asn Lys Lys Asn Ser Ile Asn Gly Cys
    450                 455                 460

<210> SEQ ID NO 3
<211> LENGTH: 1910
<212> TYPE: DNA
<213> ORGANISM: Hordeum vulgare
<220> FEATURE:
<221> NAME/KEY: CDS
<222> LOCATION: (76)..(1728)

<400> SEQUENCE: 3
cgcgctacta gtagtattcc tggtgtagtc tagtagtact ctcctcctcc tccttctcct      60
cctacccgtt tcctc atg gcc acc gta cgc cag agc gac gga gtc gcc gcg     111
               Met Ala Thr Val Arg Gln Ser Asp Gly Val Ala Ala
                 1               5                  10 aac ggc ctt gcc gtg gcc gca gcc gcg aac ggc aag agc aac ggc cat     159
Asn Gly Leu Ala Val Ala Ala Ala Ala Asn Gly Lys Ser Asn Gly His
             15                  20                  25 ggc gtg gct gcc gcc gtg aac ggc aag agc aac ggc cat ggc gtg gat     207
Gly Val Ala Ala Ala Val Asn Gly Lys Ser Asn Gly His Gly Val Asp
         30                  35                  40 gcc gac gcg aac ggc aag agc aac ggc cat ggc gtg gct gcc gac gcg     255
Ala Asp Ala Asn Gly Lys Ser Asn Gly His Gly Val Ala Ala Asp Ala
 45                  50                  55                  60 aac ggc aag agc aac ggc cat gcc gag gcc act gcg aac ggc cac ggc     303
Asn Gly Lys Ser Asn Gly His Ala Glu Ala Thr Ala Asn Gly His Gly
                 65                  70                  75 gag gcc act gcg aac ggc aag acc aac ggc cac cgc gag agc aac ggc     351
Glu Ala Thr Ala Asn Gly Lys Thr Asn Gly His Arg Glu Ser Asn Gly
             80                  85                  90
```

```
                                                    -continued
cat gct gag gcc gcc gac gcg aac ggc gag agc aac gag cat gcc gag    399
His Ala Glu Ala Ala Asp Ala Asn Gly Glu Ser Asn Glu His Ala Glu
        95                  100                 105 gac tcc gcg gcg aac ggc gag agc aac ggg cat gcg gcg gcg gca        447
Asp Ser Ala Ala Asn Gly Glu Ser Asn Gly His Ala Ala Ala Ala
110                 115                 120 gag gag gag gag gcg gtg gag tgg aat ttc gcg ggt gcc aag gac ggc    495
Glu Glu Glu Glu Ala Val Glu Trp Asn Phe Ala Gly Ala Lys Asp Gly
125                 130                 135                 140 gtg ctg gcg gcg acg ggg gcg aac atg agc atc cgg gcg ata cgg tac    543
Val Leu Ala Ala Thr Gly Ala Asn Met Ser Ile Arg Ala Ile Arg Tyr
                145                 150                 155 aag atc agc gcg agc gtg cag gag aag ggg ccg cgg ccc gtg ctg ccg    591
Lys Ile Ser Ala Ser Val Gln Glu Lys Gly Pro Arg Pro Val Leu Pro
                160                 165                 170 ctg gcc cac ggg gac ccg tcc gtg ttc ccg gcc ttc cgc acg gcc gtc    639
Leu Ala His Gly Asp Pro Ser Val Phe Pro Ala Phe Arg Thr Ala Val
                175                 180                 185 gag gcc gag gac gcc gtc gcc gcc gcc gtg cgc acc ggc cag ttc aac    687
Glu Ala Glu Asp Ala Val Ala Ala Ala Val Arg Thr Gly Gln Phe Asn
190                 195                 200 tgc tac ccc gcc ggc gtc ggc ctc ccc gcc gca cga agc gcc gtg gca    735
Cys Tyr Pro Ala Gly Val Gly Leu Pro Ala Ala Arg Ser Ala Val Ala
205                 210                 215                 220 gag cac ctg tcg cag ggc gtg ccg tac atg cta tcg gcc gac gac gtc    783
Glu His Leu Ser Gln Gly Val Pro Tyr Met Leu Ser Ala Asp Asp Val
                225                 230                 235 ttc ctc acc gcc ggc ggg acc cag gcg atc gag gtc ata atc ccg gtg    831
Phe Leu Thr Ala Gly Gly Thr Gln Ala Ile Glu Val Ile Ile Pro Val
                240                 245                 250 ctg gcc cag acc gcc ggc gcc aac att ctg ctc ccc agg cca ggc tac    879
Leu Ala Gln Thr Ala Gly Ala Asn Ile Leu Leu Pro Arg Pro Gly Tyr
                255                 260                 265 cca aac tac gag gcg cgc gcc gcg ttc aac agg ctg gag gtc cgg cat    927
Pro Asn Tyr Glu Ala Arg Ala Ala Phe Asn Arg Leu Glu Val Arg His
                270                 275                 280 ttc gac ctc atc ccc gac aag ggg tgg gag atc gac atc gac tcg ctg    975
Phe Asp Leu Ile Pro Asp Lys Gly Trp Glu Ile Asp Ile Asp Ser Leu
285                 290                 295                 300 gaa tcc atc gcc gac aag aac acc acc gcc atg gtc atc ata aac ccc    1023
Glu Ser Ile Ala Asp Lys Asn Thr Thr Ala Met Val Ile Ile Asn Pro
                305                 310                 315 aac aac ccg tgc ggc agc gtt tac tcc tac gac cat ctg tcc aag gtc    1071
Asn Asn Pro Cys Gly Ser Val Tyr Ser Tyr Asp His Leu Ser Lys Val
                320                 325                 330 gcg gag gtg gcg aaa agg ctc gga ata ttg gtg att gct gac gag gta    1119
Ala Glu Val Ala Lys Arg Leu Gly Ile Leu Val Ile Ala Asp Glu Val
                335                 340                 345 tac ggc aag ctg gtt ctg ggc agc gcc ccg ttc atc cca atg gga gtg    1167
Tyr Gly Lys Leu Val Leu Gly Ser Ala Pro Phe Ile Pro Met Gly Val
            350                 355                 360 ttt ggg cac atc acc cct gtg ctg tcc ata ggg tct ctg tcc aag tca    1215
Phe Gly His Ile Thr Pro Val Leu Ser Ile Gly Ser Leu Ser Lys Ser
365                 370                 375                 380 tgg ata gtg cct gga tgg cgg ctt gga tgg gta gcg gtg tac gac ccc    1263
Trp Ile Val Pro Gly Trp Arg Leu Gly Trp Val Ala Val Tyr Asp Pro
                385                 390                 395 aga aag atc tta cag gaa act aag atc tct aca tca att acg aat tac    1311
Arg Lys Ile Leu Gln Glu Thr Lys Ile Ser Thr Ser Ile Thr Asn Tyr
                400                 405                 410
```

-continued

```
ctc aat gtc tcg aca gac cca gca acc ttc att cag gca gct ctt cct    1359
Leu Asn Val Ser Thr Asp Pro Ala Thr Phe Ile Gln Ala Ala Leu Pro
        415                 420                 425 cag att ctt gag aac aca aag gaa gat ttc ttt aag gcg att att ggt    1407
Gln Ile Leu Glu Asn Thr Lys Glu Asp Phe Phe Lys Ala Ile Ile Gly
    430                 435                 440 ctg cta aag gaa tca tca gag ata tgc tac aaa caa ata aag gaa aac    1455
Leu Leu Lys Glu Ser Ser Glu Ile Cys Tyr Lys Gln Ile Lys Glu Asn
445                 450                 455                 460 aaa tac att aca tgt cct cac aag cca gaa gga tca atg ttt gtc atg    1503
Lys Tyr Ile Thr Cys Pro His Lys Pro Glu Gly Ser Met Phe Val Met
                465                 470                 475 gtg aaa ctg aac tta cat ctt ttg gag gaa ata gac gat gac att gat    1551
Val Lys Leu Asn Leu His Leu Leu Glu Glu Ile Asp Asp Asp Ile Asp
            480                 485                 490 ttt tgc tgc aag ctc gca aaa gaa gaa tca gta atc tta tgc cca ggg    1599
Phe Cys Cys Lys Leu Ala Lys Glu Glu Ser Val Ile Leu Cys Pro Gly
        495                 500                 505 agt gtt ctt gga atg gca aac tgg gtc cgc att act ttt gct tgt gtt    1647
Ser Val Leu Gly Met Ala Asn Trp Val Arg Ile Thr Phe Ala Cys Val
    510                 515                 520 cca tct tct ctt caa gat ggt ctc gga agg atc aaa tca ttc tgt caa    1695
Pro Ser Ser Leu Gln Asp Gly Leu Gly Arg Ile Lys Ser Phe Cys Gln
525                 530                 535                 540 agg aac aag aag aga aat tcg agc gat gat tgc tagttgtata tctgactgaa  1748
Arg Asn Lys Lys Arg Asn Ser Ser Asp Asp Cys
                545                 550 gctgtaaatc attcccagta tccccatcta tatctttcaa taaaatggaa cttttagttc  1808
tctatgaata gaagtcaaca tctccttgaa tatgttctgg ttgttgtggc ctggacgaaa  1868
catagtgaat gttatgttag tgaagttaaa aaaaaaaaaa aa                     1910

<210> SEQ ID NO 4
<211> LENGTH: 551
<212> TYPE: PRT
<213> ORGANISM: Hordeum vulgare

<400> SEQUENCE: 4

Met Ala Thr Val Arg Gln Ser Asp Gly Val Ala Ala Asn Gly Leu Ala
  1               5                  10                  15

Val Ala Ala Ala Asn Gly Lys Ser Asn Gly His Gly Val Ala Ala
             20                  25                  30

Ala Val Asn Gly Lys Ser Asn Gly His Gly Val Asp Ala Asp Ala Asn
         35                  40                  45

Gly Lys Ser Asn Gly His Gly Val Ala Ala Asp Ala Asn Gly Lys Ser
     50                  55                  60

Asn Gly His Ala Glu Ala Thr Ala Asn Gly His Gly Glu Ala Thr Ala
 65                  70                  75                  80

Asn Gly Lys Thr Asn Gly His Arg Glu Ser Asn Gly His Ala Glu Ala
                 85                  90                  95

Ala Asp Ala Asn Gly Glu Ser Asn Glu His Ala Glu Asp Ser Ala Ala
            100                 105                 110

Asn Gly Glu Ser Asn Gly His Ala Ala Ala Ala Glu Glu Glu Glu
        115                 120                 125

Ala Val Glu Trp Asn Phe Ala Gly Ala Lys Asp Gly Val Leu Ala Ala
    130                 135                 140

Thr Gly Ala Asn Met Ser Ile Arg Ala Ile Arg Tyr Lys Ile Ser Ala
```

-continued

```
            145                 150                 155                 160
Ser Val Gln Glu Lys Gly Pro Arg Pro Val Leu Pro Leu Ala His Gly
                165                 170                 175
Asp Pro Ser Val Phe Pro Ala Phe Arg Thr Ala Val Glu Ala Glu Asp
            180                 185                 190
Ala Val Ala Ala Val Arg Thr Gly Gln Phe Asn Cys Tyr Pro Ala
            195                 200                 205
Gly Val Gly Leu Pro Ala Ala Arg Ser Ala Val Ala Glu His Leu Ser
            210                 215                 220
Gln Gly Val Pro Tyr Met Leu Ser Ala Asp Val Phe Leu Thr Ala
225                 230                 235                 240
Gly Gly Thr Gln Ala Ile Glu Val Ile Ile Pro Val Leu Ala Gln Thr
                245                 250                 255
Ala Gly Ala Asn Ile Leu Leu Pro Arg Pro Gly Tyr Pro Asn Tyr Glu
            260                 265                 270
Ala Arg Ala Ala Phe Asn Arg Leu Glu Val Arg His Phe Asp Leu Ile
            275                 280                 285
Pro Asp Lys Gly Trp Glu Ile Asp Ile Asp Ser Leu Glu Ser Ile Ala
        290                 295                 300
Asp Lys Asn Thr Thr Ala Met Val Ile Ile Asn Pro Asn Asn Pro Cys
305                 310                 315                 320
Gly Ser Val Tyr Ser Tyr Asp His Leu Ser Lys Val Ala Glu Val Ala
                325                 330                 335
Lys Arg Leu Gly Ile Leu Val Ile Ala Asp Glu Val Tyr Gly Lys Leu
            340                 345                 350
Val Leu Gly Ser Ala Pro Phe Ile Pro Met Gly Val Phe Gly His Ile
            355                 360                 365
Thr Pro Val Leu Ser Ile Gly Ser Leu Ser Lys Ser Trp Ile Val Pro
        370                 375                 380
Gly Trp Arg Leu Gly Trp Val Ala Val Tyr Asp Pro Arg Lys Ile Leu
385                 390                 395                 400
Gln Glu Thr Lys Ile Ser Thr Ser Ile Thr Asn Tyr Leu Asn Val Ser
                405                 410                 415
Thr Asp Pro Ala Thr Phe Ile Gln Ala Ala Leu Pro Gln Ile Leu Glu
            420                 425                 430
Asn Thr Lys Glu Asp Phe Phe Lys Ala Ile Ile Gly Leu Leu Lys Glu
            435                 440                 445
Ser Ser Glu Ile Cys Tyr Lys Gln Ile Lys Glu Asn Lys Tyr Ile Thr
450                 455                 460
Cys Pro His Lys Pro Glu Gly Ser Met Phe Val Met Val Lys Leu Asn
465                 470                 475                 480
Leu His Leu Leu Glu Glu Ile Asp Asp Ile Asp Phe Cys Cys Lys
            485                 490                 495
Leu Ala Lys Glu Glu Ser Val Ile Leu Cys Pro Gly Ser Val Leu Gly
                500                 505                 510
Met Ala Asn Trp Val Arg Ile Thr Phe Ala Cys Val Pro Ser Ser Leu
            515                 520                 525
Gln Asp Gly Leu Gly Arg Ile Lys Ser Phe Cys Gln Arg Asn Lys Lys
            530                 535                 540
Arg Asn Ser Ser Asp Asp Cys
545                 550
```

<210> SEQ ID NO 5

-continued

```
<211> LENGTH: 23
<212> TYPE: DNA
<213> ORGANISM: Artificial Sequence
<220> FEATURE:
<223> OTHER INFORMATION: Description of Artificial Sequence:primer 1
<220> FEATURE:
<221> NAME/KEY: modified_base
<222> LOCATION: (1)..(23)
<223> OTHER INFORMATION: n=inosine

<400> SEQUENCE: 5
gcngtngart ggaayttygc nmg                                     23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer 2
<220> FEATURE:
<221> NAME/KEY: modified_base
<222> LOCATION: (1)..(20)
<223> OTHER INFORMATION: n=inosine

<400> SEQUENCE: 6
gcdatrtgnc craanacncc                                         20

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:dt17 adapter
      primer

<400> SEQUENCE: 7
gactcgagtc gacatcgatt tttttttttt ttttt                        35
```